(12) United States Patent
Code et al.

(10) Patent No.: US 8,846,067 B2
(45) Date of Patent: Sep. 30, 2014

(54) ANTIMICROBIAL SOLUTIONS AND METHODS

(71) Applicants: Kenneth R. Code, Edmonton (CA); Joseph Provenzano, Huntington Beach, CA (US); Richard D. Bickerstaff, Phoenix, AZ (US)

(72) Inventors: Kenneth R. Code, Edmonton (CA); Joseph Provenzano, Huntington Beach, CA (US); Richard D. Bickerstaff, Phoenix, AZ (US)

( * ) Notice: Subject to any disclaimer, the term of this patent is extended or adjusted under 35 U.S.C. 154(b) by 11 days.

(21) Appl. No.: 13/843,615

(22) Filed: Mar. 15, 2013

(65) Prior Publication Data

US 2013/0287865 A1  Oct. 31, 2013

Related U.S. Application Data

(63) Continuation-in-part of application No. 13/308,105, filed on Nov. 30, 2011, now Pat. No. 8,642,057, and a continuation-in-part of application No. 12/009,586, filed on Jan. 18, 2008, now Pat. No. 8,226,964.

(60) Provisional application No. 61/490,448, filed on May 26, 2011.

(51) Int. Cl.
  *A01N 25/00* (2006.01)
  *A01N 59/12* (2006.01)

(52) U.S. Cl.
  CPC ...................................... *A01N 59/12* (2013.01)

USPC .......................................................... 424/405

(58) Field of Classification Search
  USPC ......... 424/408, 417–420, 455, 490–495, 637, 424/638, 667–671; 514/608, 962, 963
  See application file for complete search history.

(56) References Cited

U.S. PATENT DOCUMENTS

| | | |
|---|---|---|
| 3,516,941 A | 6/1970 | Matson |
| 3,860,565 A | 1/1975 | Barber, Jr. |
| 4,056,610 A | 11/1977 | Barber, Jr. et al. |
| 4,756,906 A | 7/1988 | Sweeny |
| 5,433,953 A | 7/1995 | Tsuei |
| 5,589,194 A | 12/1996 | Tsuei |
| 5,804,298 A | 9/1998 | Moy |
| 6,413,548 B1 | 7/2002 | Hamer |
| 7,867,510 B2 * | 1/2011 | Code .............................. 424/443 |
| 2003/0194447 A1 * | 10/2003 | Scholz et al. ................. 424/672 |
| 2009/0226541 A1 * | 9/2009 | Scholz et al. ................. 424/672 |

* cited by examiner

*Primary Examiner* — Anand Desai
*Assistant Examiner* — Melissa Mercier
(74) *Attorney, Agent, or Firm* — Mark A. Litman & Associates, P.A.

(57) ABSTRACT

Antimicrobial solutions and delivery systems for them use liquid antimicrobial solutions with: at least 80% of total weight of a carrier liquid comprising water, alcohol or a mixture of water and alcohol; at least 0.0001% by weight of the solution of $I_2$; at least 0.0001% by weight of $CuSO_4$; and sufficient acid in the solution top provide a pH of less than 7.0. A buffering system is also preferable in the solution, and the solution may be provided directly to wounds, burns or other skin damage as a liquid, as a spray or as a gel.

13 Claims, No Drawings

ANTIMICROBIAL SOLUTIONS AND METHODS

RELATED APPLICATIONS DATA

This application claims priority as a continuation-in-part application of U.S. patent application Ser. No. 13/308,105 filed 30 Nov. 2011, which is in turn a continuation-in-part application under 35 U.S.C. 120 from U.S. patent application Ser. No. 12/009,586, filed Jan. 18, 2008. The present application also claims priority from Provisional U.S. patent application Ser. No. 61/490,448, filed May 26, 2011.

BACKGROUND OF THE INVENTION

1. Field of the Invention

The present invention relates to the field of antimicrobial solutions, anti-odor solutions and delivery systems for the solutions.

2. Background of the Art

Iodine solutions have been used for over a century as a disinfectant. Further advances in the performance and stability of iodine solutions are desirable.

SUMMARY OF THE INVENTION

A liquid antimicrobial solution is provided which may contain by way of non-limiting examples:

A liquid antimicrobial solution comprising:
at least 80% of total weight of a carrier liquid comprising water, alcohol or a mixture of water and alcohol;
at least 0.001% by weight of the solution of $I_2$; and sufficient acid in the solution to provide a pH of less than 6.5.

Another description is a solution as:
at least 80% of total weight of a carrier liquid comprising water, alcohol or a mixture of water and alcohol;
at least 0.0005% by weight of the solution of I2 (e.g., at least 10, at least 15 or at least 20 ppm) and/or and
sufficient acid in the solution to provide a pH of less than 6.5.

An alternative solution may contain, by way of non-limiting examples:
0.001% by weight (or at least 10 ppm of the solution) of the solution of a cation (e.g., $K^+$) and a solution of $I_2$ (and some residual F);
at least 0.001% by weight of $CuSO_4$; and
sufficient acid in the solution to provide a pH of less than 6.5.

These solutions of the present invention may be provided in numerous formats.

DETAILED DESCRIPTION OF THE INVENTION

One aspect of technology described herein includes a liquid antimicrobial solution with:
A) at least 80% of total weight of a carrier liquid comprising water, alcohol or a mixture of water and alcohol;
at least 0.0005% by weight of the solution of $I_2$; (e.g., 0.0005 to 0.10% by weight, 10-100 ppm, 10-80 ppm, 10-50 ppm, 10-30 ppm iodine), and/or E and sufficient acid (even with buffering) in the solution to provide a pH of less than 7.0, preferably less than 6.5; or
B) at least 80% of total weight of a carrier liquid comprising water and dissolved iodine, alcohol or a mixture of water and alcohol;
at least 0.001% by weight of the solution of ($I_2$ (e.g., 0.0005 to 0.10% by weight, 10-100 ppm, 10-80 ppm, 10-50 ppm, 10-30 ppm iodine), and/or F;) and cation (e.g., $K^+$) and residual, non-critical, equilibrium E;
at least 0.001% by weight of of the solution of $CuSO_4$; and
sufficient acid in the solution top provide a pH of less than 5.0.

The solution may have acid in sufficient amount to provide an initial pH of from 2.0 to 4.8 or 3.5 to 6.0, and then be buffered to moderate the pH to a less acidic (but still acidic) level. The solution has a preferred acid of sulfamic acid and may then be buffered back to a pH of 5.8-7.0, preferably 6.0-6.5.

The solutions of the present technology may be provided, by way of non-limiting examples, wherein the acid is sufficient in an amount to provide a pH of from 5.5 to 6.7, especially where the acid comprises a sulfamic acid compound, such as a sulfamic acid compound having the formula:

wherein R is independently selected from the group consisting of hydrogen and electron-withdrawing groups, or a sulfamic acid compound having the formula:

wherein R is independently selected from the group consisting of hydrogen, halogen, cyano, C1-C6 alkyl, C1 to C6 substituted alkyl, perhalo alkyl, halosubstituted alkyl, and electron-withdrawing groups.

One embodiment may have least one R as hydrogen, or exactly one R as hydrogen. A spherical encapsulation system may be provided as a core of liquid comprising the solution of the present technology having at least 5% by weight water therein, and an encapsulant surrounding the core to form stable encapsulated particles, the encapsulant comprising at least one layer of hydrophobic particles in contact with and surrounding the core, the core and hydrophobic particles providing an encapsulated system that has a volume weighted mean particle diameter of from 0.05 to 25 micrometers, at least 25% of the spherical encapsulated system is spherical and can support its own weight. For example, the encapsulation system may have the core as a droplet of the solution having a diameter of from 0.0001 to 1 mm. The encapsulation system may have the droplet of solution comprises 10-90% average percentage by weight of the encapsulation system.

Another encapsulation system comprising droplet cores of aqueous liquids comprising the solution of the present technology having diameters of from 0.0001 to 0.5 mm of aqueous liquid having a surface, said droplets having a stabilizing layer comprising hydrophobic particles with a volume weighted mean particle diameter of from 0.05 to 25 micrometer hydrophobic particles on said surface, said stabilizing layers being generally spherical, with at least 25% by number of all droplets encapsulated by hydrophobic particles in said encapsulated system having less than a 25% deviation in diameter in cross-sections. The layer of hydrophobic particles may be a layer of particles with less than 80% by number of said particles being bonded to any adjacent particle.

One additional subgeneric format includes a microencapsulated particles comprising a frangible shell having a liquid core of the solution of the present technology. The frangible shell may be a polymer and the microencapsulated particles have a number average diameter of 0.001 to 2 mm (or larger, such as up to 5 mm).

Another additional subgeneric format includes an iodine delivery system comprising a hydrocolloid entraining at least 20 by weight of the delivery system of the solution of the present technology.

Still another iodine delivery system includes a clay entraining at least 20 by weight of the delivery system of the solution of the present technology or an iodine delivery system comprising a flexible polymer having droplets of the solution of the technology disclosed herein dispersed therein. This last iodine delivery system may have the droplets with a number average diameter of 0.001 to 2 mm.

The present solution technology may be delivered in a variety of different formats, depending upon the specific use and needs of individual environments and technical applications. The material may be directly applied as a liquid, or brought in a protected mode (e.g., so the liquid solution does not immediately flow (e.g., encapsulated, gelled, imbibed, entrained, etc.). The following descriptions are examples of specific embodiments within the scope of the generic invention.

1. Gel With Iodine and Boron to Control Radiation Leaks

This aspect of the technology prescribes that the chemical basis of nuclear fuel control rods (boron from boric acid, hafnium, cadmium) be suspended in our CupriDyne-SAP™ gel to a desired consistency without breaking the gel, and then disposing on spent fuel rods, fuel rods, and other nuclear plant containment vessels and areas, to absorb neutrons, and cool down the target. This is useful when water cannot be used, but desirable also in that the flocculent of SAP will acquire the fission products as well, and prevent exposure to alpha, beta, and most gamma rays. Just as firefighting using fire retardant chemicals is dropped from the air, likewise a gel will adhere to all surfaces to cool down the spill or problem rods. In essence, it is a gelled version of a control rod which can be pumped by emergency pumpers. Water with boric acid has been tried by the Japanese, but the amount of boric acid is limited to 3-5%, especially in sea water—not enough to cool down the fuel rods, and then the water leaked out from containment in the particular instance, anyway.

Other organic and inorganic polymers and thixotropic agents may be used to increase the viscosity of the solutions or even gel the solutions. Silicas, acrylics, clays, natural resins and oils and waxes, viscofiers and other known additives may be used alone or in combination with stabilizing or emulsifying agents to form solutions, thick solutions, gels of other flowable compositions. Additional polymers and additives such as cellulosic materials (e.g., carboxy alkyl celluloses, such as carboxy methyl cellulose), polyalkylene glycols, phthalates, alcohols, dyes, indicators and the like can be used in the solutions.

2. Stable Iodine Liquid Compositions/Solutions (Ready to Use and Concentrate)

An iodine solution is acidified by the addition of an acid that (alone) produces a pH of less than 6.7 at 1.0 N in deionized water and preferably less than 6.5 under those parameters. Typical acids may be organic acids, inorganic acids, Lewis acids, HCl, HI, HBr (halogenic acids), $HNO_3$, $HClO_4$, $H_2SO_4$, $H_2SO_3$, and especially the family of sulfamic acids.

The iodine environment can be provided in numerous and varied tasks and services and even in combination with other additives such as stable active solutions or film-breaking compositions such as acids (e.g., sulfamic acid, hydrochloric acid, sulfuric acid, enzymes, etc.). At present, the most widely known and accepted acidizing agents include HCl, sulfamic acid, lactic acid, citric acid, and acetic acid, all with varying degrees of reactivity for descaling. The effect of acidizing with iodine gas in solution, however, also attends with additive antimicrobial effects, and when the acidized iodine is combined with sulfamic acid, a powerful and effective method is provided for dissolving and remediating biofilms, and chelating heavy metals which may be solubilized by the process, or otherwise contained in water, especially after physical disruption as described herein.

Sulfamic acid is also a primitive surfactant, and when added to free iodine in water and stabilized by varying added compounds such as silicates (e.g., sodium metasilicate) and phosphates and sulfonates (e.g., sodium xylene sulfonate or phosphate), yields a disinfecting and biofilm removing detergent compound which is active within the technologies described herein for oilfield or watershed applications as a single formulary product. The term a "sulfamic acid compound" or a member of the family of sulfamic acids or class of sulfamic acids is herein defined as any sulfamic acid central moiety with a single substituent on the amide group of the sulfamic acid moiety or sulfamic acid core structure that still allows the sulfamic acid derivative in the family of sulfamic acids to display a pH of less than 6.8 at 0.5N in deionized water, preferably less than 6.5 under those parameters (e.g., 5.5 to 6.7, 5.5 to 6.2, and 4.0-6.7, and 3.0 to 6.7 and even lower levels of acidity up to 6.5, up to 6.6 or up to 6.7 pH). As non-limiting examples of these known sulfamic acid family compounds are sulfamic acid, iodosulfamic acid, chlorosulfamic acid, bromosulfamic acid, fluorosulfamic acid, alkylsulfamic acid (with C1-C8 carbon groups, whether linear, branched or cyclic, such as cycloheylsulfamic acid, and substituted or not, such as trifluromethylsulfamic acid, pentachloroethylsulfamic acid, etc.), cyanosulfamic acid, any electron-withdrawing group on the amide position of the sulfamic acid and even lightly electron-donating groups that do not change the sulfamic acid from an acid to a base at 1.0N in deionized water.

The formula for sulfamic acid is $NH_2SO_3H$ and the corresponding formula for a sulfamic acid compound is represented by:

$NR_2SO_3H$, wherein R is independently selected from the groups described above, such as hydrogen, halogen, cyano, C1-C6 alkyl or substituted alkyl, perhalo alkyl, halosubstituted alkyl, electron-withdrawing groups, mild electron-donating groups and the like. It is preferred that at least one R group is hydrogen.

The inventor has noted that the addition of sulfamic acid (in particular) to all CupriDyne198 treatment composition formulas can provide ultimate stability or even enhanced activity in its various antimicrobial or surface treatment procedures. The sulfamic acid is both an acidifying agent (and other acids may be used) and a primitive surfactant. CupriDyne™ antimicrobial compositions in water is stabilized (free iodine is continuously available) by lowering pH to 5.5-6.7. Even the CuI resulting component is held in solution. The addition of surfactants, such as sodium metasilicate and sodium tripolyphosphate assists in completing a detergent preparation formula. The solutions may have normal levels of iodine therein (e.g., at least 5 ppm or may be concentrated for dilution with greater than 50 ppm, greater than 100 ppm, greater than 200 ppm, up to solubility limits of iodine in aqueous or alcohol solvents.

The solution is preferred where the acid comprises a sulfamic acid compound having the formula:

wherein R is independently selected from the group consisting of hydrogen and electron-withdrawing groups. The acid may comprise a sulfamic acid compound having the formula:

wherein R is independently selected from the group consisting of hydrogen, halogen, cyano, C1-C6 alkyl, C1 to C6 substituted alkyl, perhalo alkyl, halosubstituted alkyl, and electron-withdrawing groups.

The solution may have at least one R is hydrogen in the sulfamic acid compound or only and exactly one R is hydrogen.

These solutions are antimicrobial, have anti-odor effects, and can bleach or remove some stains.

The solutions have been found to be even further improved by buffering to keep the pH of the solution within an optimum range of between 5.8-7.5, more preferably between 5.8 and 6.5, and still more preferably between 6.0 and 6.4. Preferred buffering agents include inorganic cation buffering agents such as carbonates, bicarbonates, phosphates and other inorganic basic salts. Sodium, calcium, potassium and lithium salts of the buffering agents are preferred, but ammonium salts may also be used. The buffering of the solution surprisingly adds significant value to the solutions including at least one of storage stability, aerial stability, reduced cell toxicity, reduced corrosiveness, reduced corrosive action on dentures and bone and the like.

It has also been found that the order of mixing certain combinations of ingredients simplifies the dissolution of individual ingredients and improves some final solutions properties (such as transparency). For example, it has been found that first dissolving the buffering agent or the acid, and then dissolving the acid or buffering agent, respectively, makes it easier to dissolve the active components and make it easier to provide a transparent active iodine solution. The two iodine-forming reactive ingredients may then be added into the acid-buffer solution. The $CuSO_4$ may be first dissolved into the acid-buffer solution and then the alkali or alkaline iodide is dissolved in the acid-buffer/$CuSO_4$ solution. The iodide may be added as Li, Na, K, Ca, Mg, $NH_4$ iodide or the like. In certain medical and environmental uses, the selection of the particular cation may be more than merely a matter of convenience or choice of equivalents. The particular cation may be desirable as Na in certain medical applications where Li or K is less desirable. The various cations may be selected for design and concentration to maintain an appropriate isotonic balance with patients and their cells and vessels. The concentration of the cations and anions and iodine in solution, the pH and the selection of particular incidental cations and anions are selected to achieve balances of properties in the solutions.

The solutions of the present technology may be added to, combined with and/or modified to replicate other known medical solutions, as with the case of "Normal" saline, where 0.9% w/w NaCl in sterile water is involved, so that it is possible to compute the Na content to include a change from KI to NaI in this technology. This can be used to create a solution with 260 to 310 mOsm/L osmolality, or preferably between 275 and 300 mOsm/L osmolality, and approach balance with the normal Na or cation pressure in tissue. In one preferred embodiment, sodium iodide replaces portions of (5%, 10%, 20%, 30%, 50%, 60%, 75%, 80%, 90%, 95%) or all of the potassium iodide.

On another level, a lactated Ringer's solution is possible. "One liter of lactated Ringer's solution ordinarily contains:
  130 mEq (80-200) of sodium ion=130 mmol/L
  109 mEq (70-180) of chloride ion=109 mmol/L
  28 mEq (15-50) of lactate=28 mmol/L
  4 mEq (2-8) of potassium ion=4 mmol/L
  3 mEq (1.5-4) of calcium ion=1.5 mmol/L"
An equivalent or partial replacement equivalent or mixture with solutions according to the present technology may also be prepared. The sodium, chloride, potassium, calcium and chloride in the standard lactated Ringer's solution may vary among each other by percentages n the order of (5%, 10%, 20%, 30%, 50%, 60%, 75%, 80%, 90%, and 95%) among each other.

These stable solutions are advantageously deliverable in many different forms, besides direct liquid delivery as a wipe, spray or brush application. For example, the solutions may be provided as a spherical encapsulation system comprising a core of liquid comprising the solution of the present technology having at least 5% by weight water therein, and an encapsulant surrounding the core to form stable encapsulated particles, the encapsulant comprising at least one layer of hydrophobic particles in contact with and surrounding the core, the core and hydrophobic particles providing an encapsulated system that has a volume weighted mean particle diameter of from 0.05 to 25 micrometers, at least 25% of the spherical encapsulated system is spherical and can support its own weight. The core may, for example, comprise a droplet of the solution having a diameter of from 0.0001 to 1 mm. The encapsulation system may have the droplet of solution comprises 10-90% average percentage by weight of the encapsulation system. These solutions may be directly applied, sprayed, imbibed in a fabric carrier and applied as a wipe, or gelled and the like.

3. Encapsulated or Microencapsulated Delivery Systems

Another format is as an encapsulation system comprising droplet cores of aqueous liquids comprising the solution of the present technology having diameters of from 0.0001 to 0.5 mm of aqueous liquid having a surface, said droplets having a stabilizing layer comprising hydrophobic particles with a volume weighted mean particle diameter of from 0.05 to 25 micrometer hydrophobic particles on said surface, said stabilizing layers being generally spherical, with at least 25% by number of all droplets encapsulated by hydrophobic particles in said encapsulated system having less than a 25% deviation in diameter in cross-sections. The layer of hydrophobic particles may comprise a layer of particles with less than 80% by number of said particles being bonded to any adjacent particle. This technology is enabled in U.S. Pat. No. 6,413,548. By this technology, generally non-compatible materials may be provided from a single delivery system by a unique encapsulation system. An encapsulation system is advantageously constructed as a core of aqueous liquid having at least 5% by weight water therein, and an encapsulant surrounding the core to form a stable encapsulated particle, the encapsulant comprising at least one layer of hydrophobic particles in contact with and surrounding the core, the core and hydrophobic particles providing an encapsulated system that has an average weight average particle diameter of from 0.05 to 25 micrometers and can support its own weight. The encapsulation system may be provided by a novel method of manufacture comprising providing a mass of hydrophobic particles having average mass diameter size of between 0.05 and 25 micrometers, providing droplets of an aqueous medium to the mass of particles, gently mixing the fine particles of aqueous medium and the hydrophobic particles to form a stable encapsulant system of droplets of the aqueous medium encapsulated by a shell of particles.

Another format of liquid solution delivery is as a microencapsulated particles comprising a frangible shell having a liquid core of the solution of the present technology. The microencapsulated particles may have a frangible shell that comprises a polymer and the microencapsulated particles have a number average diameter of 0.001 to 2 mm. Such technology for forming the shells with liquid fill is enabled as microcapsules produced through interfacial polymerization having shell walls composed of polyamides, polyureas, polyurethanes, and polyesters are known; see U.S. Pat. Nos. 3,516,941, 3,860,565, 4,056,610, and 4,756,906. Alternative enabling methods include U.S. Pat. Nos. 5,433,953, 5,589,194; and 5,804,298.

4. Entrained Solution Delivery Systems

Another iodine delivery system may be as a hydrocolloid entraining at least 20 by weight of the delivery system of the solution of the present technology or as an iodine delivery system comprising a clay entraining at least 20 by weight of the delivery system of the solution of the present technology.

5. Aqueous Solution Entrapped in Polymeric Medium

Another alternative liquid delivery system may be as an iodine delivery system comprising a flexible polymer having droplets of the solution of the present technology dispersed therein. This form of liquid delivery system, may for example, use droplets have a number average diameter of 0.001 to 2 mm.

Droplets of aqueous solution may be suspended, dispersed or emulsified within a hardenable (driable or polymerizable) film forming polymeric composition. The hardenable film-forming polymer (which is inclusive of elastomers) is then hardened by driving off solvents (drying) or polymerizing the solution or neat (little or no solvent) polymerizable composition to stably entrain the droplets of solution within the hardened film. Rather than droplets, frangible microcapsules or water-beads as disclosed in U.S. Pat. No. 6,413,548 (cited above) may be blended into the hardenable polymeric composition, which is then hardened.

The liquids and stabilized (e.g., encapsulated) liquid solutions of the present technology may be used in a wide variety of environments. The liquid solutions may be applied directly to surfaces such as surgical tables, surgical tool trays, surgical tools, surgical tubing; dental tools; equestrian wares such as bits, spurs, metal harness loops, silverware, kitchen sinks and cooking tools; animal sheds, animal coup walls and floors and the like. The encapsulated or stabilized solutions may be added to a wide range of products to add antimicrobial or antiodor properties to otherwise conventional products such as papers, napkins, placemats, animal bedding, animal litter, bandages, wraps, sanitary napkins, wound dressings, bed covers, bed pads, transportation wrappings for food (e.g., wrapping paper for fruit, and tray covers for meat), and the like. The solutions and their delivery systems may be included in sealing waxes, seals (e.g., elastomeric tubing and joint seals and washers), animal chew toys (e.g., using the droplet distribution in the elastomer/polymer, or adding a coating layer of polymer with droplets or encapsulated solutions to provide releasable iodine solution from a surface subject to abrasion or pressure).

Frangible encapsulants of the presently described technology, when entrained in insulation media such as styrofoam or fiber batts, add phase change temperature control around the freezing point of the liquid fill. Phase-change insulation media, once frozen and packaged for infectious samples (for example) will delay a package warmup when exposed to ambient temperatures to assist with sample or specimen preservation. In the event that warmup ultimately occurs, the pre-frozen capsules which have expanded at the freezing point of aqueous fill will deploy their contents into the insulation media. The presently described iodine solutions in this format are therefore a broad spectrum oxidative countermeasure against the contents of the samples or specimens which have likely leaked their contents as well.

Similarly, the liquid solutions of the present technology, when frozen, may be provided to contain clathrates of stabilized free iodine which are active oxidizers in solution upon progressive melting. This is a countermeasure against fouling during refrigerated transportation of foods, and at ambient retail outlets with the foods on display.

One skilled in the arts related to this technology, including antiseptic and antimicrobial fields, polymer chemistry, emulsion chemistry and encapsulation technology can provide specific alternatives and equivalents within the scope of the generic disclosure and enablement disclosed herein.

Each reference cited in this disclosure are incorporated by reference in their entirety.

The solutions, gels and compositions described herein are also useful in direct medical treatment of wounds, sores, topical conditions and transdermally accessible conditions. The use of gels, solutions and compositions may be directly applied to the region of the patient (both human and non-human) where treatment is desired. As the primary ingredients (K, I, Cu and $S_4$) are biocompatible and are generally regarded as safe (GRAS) under FDA guidelines. The active components are so safe for human consumption they appear in over-the-counter and/or prescription medication presently in the marketplace. By selection of conventional carriers commonly used or developed in the future for delivery onto skin and into wounds, in combination with the solution and ingredients used in the present technology, assists in providing an effective medicinal composition.

In addition to the use of materials described above in forming the solutions, compositions and gels (especially in the absence of the solid carriers such as fabric, sheets and layers), such as ointment bases, cream bases, emollients, dimethylfulfoxide, alginates, natural and synthetic gums (agar-agar, polysiloxanes, polymeric carriers, solvents, biocompatible carriers, and the like. These direct addition compositions and solutions may be carried on a substrate or fabric, and (as incidentally occurring in the carried compositions of U.S. Published Patent Application Document No. 20120087965), but possibly in greater concentration where the composition or solution may flow out of the carrier/fabric and directly onto the skin or into the wound.

A carrying composition may comprises the active iodine-releasing, iodine-providing technology described herein which is effective in promoting antimicrobial activity here applied. Preferably said active ingredients comprise from about 0.01% to about 40% (including the liquid or gel carrier) by weight of the total carrier. The weight proportion of more preferably from about 0.05% to about 25%, and most preferably from about 1.0% to about 10.0% by weight may be used.

A liquid binder according to the invention is used in particular for dispersing the components, as explained below, and for enhancing the stability of the composition. Moreover, the liquid binder is used to adjust the concentrations of the active ingredients of the composition according to the invention. Obviously, the liquid binder has also additional properties, e.g. thickening properties, stabilizing properties, water-binding promoting properties as is well known to the person skilled in the art. These liquid binders are preferably selected from the liquid polyols, polymeric binders, fumed silica and gums or a combination thereof. Examples of suitable liquid polyols include glycerol, propylene glycol, polyethylene glycol (PEG). Examples of suitable gums include natural gums and modified (semi-synthetic) gums, for example acacia gum, gum arabic, caraya gum, gum tragacanth, xanthan gum and cellulose gum. Examples of suitable polymeric binders are polyvinyl pyrrolidone, casein or salts thereof, wherein the salts comprise a metal of Group 1 or Group 2 of the Periodic System. According to the invention, it is preferred that the liquid binder is glycerol, glycol, propylene glycol, PEG, fumed silica, a gum, or a combination thereof. In a particularly preferred embodiment of the present invention the liquid binder is a combination of a liquid polyol and a fumed silica, most preferably PEG 1500 in combination with fumed silica, in total amounts of 0.005 to 4% and 1 to 20%, respectively, based on the total weight of the composition. Most preferred is an amount of PEG 1500 from about 0.01% to about 2% by weight of the total composition, and an amount of fumed silica from about 3% to about 10% by weight of the total composition. Moreover, component (a) is preferably employed as an aqueous solution comprising the binder, said aqueous solution comprising 25-75% by weight, preferably 35-65% by weight of the binder, calculated on the basis of the total weight of the aqueous solution.

Additionally, according to the invention the pH of the composition is essential for a controlled and long lasting release of the active component, i.e. oxygen. Tests have revealed that the pH is preferably in the range of 3.5-6.9, preferably 4.0-6.5 and most preferably 4.5-6.2.

The composition according to the present invention, which is used for the treatment of open wounds and even burns (to prevent protection), may further comprise a gelatinous thickener. Typically a cellulose material, such as cellulose, sodium carboxymethylcellulose, (hydroxy)propylcellulose, methylcellulose, or ethylcellulose, is used as a thickener. Preferably sodium carboxymethylcellulose is used in the present invention, in an amount of 0.2 to 4.0 percent by weight, preferably 0.5 to 2.5 percent by weight, calculated on the total weight of the composition.

The composition may further comprise an agent that counteracts loss of moisture, and that optionally also has an antimicrobial action. Preferably a carbohydrate, more preferably an alditol, such as, for example, erythritol, arabinitol, xylitol, galacitol, sorbitol, iditol, mannitol, hepitol, or octitol, is used as the agent that counteracts the loss of moisture. In the present invention the use of alditol is preferred, typically in an amount of 0.5 to 10.0 percent by weight preferably in an amount of 1.0 to 5.0 percent by weight, calculated on the total weight of the composition.

The compositions may also contain an anti-oxidant. Examples of suitable anti-oxidants are Lipochroman-6, sodium ascorbylphosphate, or combinations thereof. Preferably the compositions contain an amount of anti-oxidant of about 0.10% to about 4.0% by weight of the total composition. In a preferred embodiment Lipochroman-6 and sodium ascorbylphosphate are used. Preferably the compositions contain from about 0.01% to about 1.0% by weight of Lipochroman-6, and from about 0.10% to about 3.00% by weight of sodium ascorbylphosphate.

The compositions and medicaments according to the present invention may additionally comprise a components selected from the group of antibiotics such as natural or synthetic antibiotics such as sulfa drugs that are used to treat bacterial and some fungal infections. Suitable sulfa drugs comprise prontosil, sulfadiazine, sulfamethizole (Thiosulfil Forte®), sulfainethoxazole (Gantanol®), sulfasalazine (Azulfidine®), sulfisoxazole (Gantrisin®), and various high-strength combinations of three sulfonamides. Preferably, the sulfa drug is sulfadiazine.

The compositions and medicaments according to the present invention my further comprise a zinc component which are beneficial in wound healing. A suitable example is zinc gluconate.

The compositions and medicaments according to the present invention further preferably comprise an agent that promotes degradation of biofilms on open wounds. Suitable agents include peroxide forming enzymes such as lactoperoxidase as is disclosed in WO 88/02600 of Poulson, incorporated by reference, and glycoproteins such as lactoferrin as disclosed in EP A 1.545.587, incorporated by reference.

The compositions according to the present invention can optionally further comprise any pharmaceutically acceptable excipient, such as, for example, colorants, (de)odorants, preservatives and the like. The composition, according to the present invention, is intended for use in the treatment of open wounds and burns. The term "open wound", as used herein, may refer to any type of tissue injury, but particularly to tissue injuries characterized by delay or complete failure of healing. Typical but non-limiting examples of such injuries are traumatic injury, including burns, injury resulting from surgery, diabetic wounds, pressure ulcers, arterial ulcers, decubitus ulcers, and venous stasis ulcers. The greatest benefits are achieved in injured tissues with compromised blood flow and oxygen supply.

The treatment of open wounds and burns according to the present invention typically comprises topical administration of the medicament or of a combination of the medicaments, containing the composition, to the open wound or burn. The medicament is preferably applied to the wounds or burns in amounts sufficient to completely cover the entire surface of the wound. In a preferred embodiment, the composition is applied to the open wound or burn, 1 to 8 times daily, more preferably 2 to 4 times daily. The treatment is continued as long as necessary to completely heal the wounds, it is applied to, or as long as beneficial effects are observed.

Although the aforementioned method of treatment generally applies, it is within the skill and within the objective of any professional, trained in the art of wound healing, to adjust the preferred amounts of the medicament and/or the frequency it is applied with, as well as the duration of the treatment, in order to optimize the efficacy for each individual patient. The materials and compositions of the invention may be applied to wounds, burns, cuts, mucosal tissue, mucosal membrane, and/or the skin for any after event medical condition or pre-event medical condition.

In another embodiment of the present invention the composition further comprises an oxygen donor stabilizing agent (component (c)). Addition of an oxygen donor stabilizing agent will result in a composition, which releases the active component in a more controlled manner and which shows a longer lasting effect. Compositions containing the oxygen stabilizing agent will further have improved stability during storage and transport under normal conditions. Preferably the oxygen donor stabilizing agent is selected from the group consisting of organic acids or their (monovalent or polyvalent) pharmaceutically acceptable salts, preferably inorganic salts wherein the cations of the salts are preferably metals selected from groups 1 or 2 of the Periodic System of the Elements, or from the group consisting of saccharides.

The invention claimed is:

1. A method of treating a wound or burn on tissue comprising applying an antimicrobial composition to the wound or burn on tissue, the antimicrobial composition comprising: at least 80% of total weight of a carrier liquid comprising water, alcohol, aqueous gel or a mixture of water and alcohol, water and aqueous gel, alcohol and aqueous gel, or water and alcohol and aqueous gel; at least 0.001% by weight of the solution of $I_2$; and at least 0.005% by weight of $CuSO_4$ and sufficient acid in the solution to provide a pH of less than 6.9 wherein the acid comprises a sulfamic acid compound having the formula: $NR_2SO_3H$, wherein R is independently selected from the group consisting of hydrogen and electron-withdrawing groups.

2. A method of treating a wound or burn on tissue comprising applying an antimicrobial composition to the wound or burn on tissue, the antimicrobial composition comprising: at least 80% of total weight of a carrier liquid comprising water, alcohol, aqueous gel or a mixture of water and alcohol, water and aqueous gel, alcohol and aqueous gel, or water and alcohol and aqueous gel; at least 0.001% by weight of the solution of $I_2$; and sufficient acid in the solution to provide a pH of less than 6.9 wherein the acid comprises a sulfamic acid compound having the formula: $NR_2SO_3H$, wherein R is independently selected from the group consisting of hydrogen, halogen, cyano, C1-C6 alkyl, C1 to C6 substituted alkyl, perhalo alkyl, halosubstituted alkyl, and electron-withdrawing groups.

3. The method of claim 2 wherein at least one R is hydrogen.

4. The method of claim 2 wherein exactly one R is hydrogen.

5. A method of treating a wound on tissue comprising applying an antimicrobial composition comprising a solution to the wound on tissue, the solution comprising:

at least 80% of total weight of a carrier liquid comprising water, alcohol, or a mixture of water and alcohol; at least 0.001% by weight of the solution of $I_2$ and at least 0.005% by weight of $CuSO_4$; and sufficient acid in the solution to provide a pH of from 5.5 to 6.7, wherein the acid comprises a sulfamic acid compound having the formula: $NR_2SO_3H$, wherein R is independently selected from the group consisting of hydrogen, halogen, cyano, C1-C6 alkyl, C1 to C6 substituted alkyl, perhalo alkyl, halosubstituted alkyl, and electron-withdrawing groups.

6. The method of claim 1 wherein the solution is carried in a gel, ointment or cream.

7. The method of claim 2 wherein the solution is distributed within a gel.

8. The method of claim 6 wherein the acid is sufficient in an amount to provide a pH of from 5.5 to 6.7; and the solution further comprising an inorganic cation and $I_2$ and at least 0.005% by weight of $CuSO_4$.

9. The method of claim 5 wherein the acid comprises sulfamic acid.

10. A method of treating a wound on tissue comprising applying an antimicrobial composition comprising a solution to the wound on tissue, the solution comprising: at least 80% of total weight of a carrier liquid comprising water, alcohol, or a mixture of water and alcohol; at least 0.001% by weight of the solution of $I_2$; and sufficient acid in the solution to provide a pH of less than 6.9 wherein the acid comprises sulfamic acid.

11. A method of treating a wound on tissue comprising applying an antimicrobial composition comprising a solution to the wound on tissue, the solution comprising: at least 80% of total weight of a carrier liquid comprising water, alcohol, or a mixture of water and alcohol; at least 0.001% by weight of the solution of $I_2$; and sufficient acid in the solution to provide a pH of from 5.5 TO 6.7 wherein the acid comprises a sulfamic acid compound having the formula: $NR_2SO_3H$, wherein R is independently selected from the group consisting of hydrogen, halogen, cyano, C1-C6 alkyl, C1 to C6 substituted alkyl, perhalo alkyl, halosubstituted alkyl, and electron-withdrawing groups.

12. The method of claim 11 wherein at least one R is hydrogen.

13. The method of claim 10 wherein the acid is sufficient in an amount to provide a pH of from 5.5 to 6.7; and the solution further comprising an inorganic cation and $I_2$ and at least 0.005% by weight of $CuSO_4$.

* * * * *